United States Patent [19]

Röhrscheid et al.

[11] Patent Number: 5,004,797

[45] Date of Patent: Apr. 2, 1991

[54] PARTLY FLUORINATED CARBOXYLIC ACIDS AND DERIVATIVES THEREOF, PROCESSES FOR THEIR PREPARATION AND THEIR USE

[75] Inventors: Freimund Röhrscheid, Kelkheim; Günter Siegemund; Jürgen Lau, both of Hofheim am Taunus, all of Fed. Rep. of Germany

[73] Assignee: Hoechst Aktiengesellschaft, Frankfurt am Main, Fed. Rep. of Germany

[21] Appl. No.: 275,405

[22] Filed: Nov. 23, 1988

[30] Foreign Application Priority Data

Nov. 24, 1987 [DE] Fed. Rep. of Germany ....... 3739796
Nov. 24, 1987 [DE] Fed. Rep. of Germany ....... 3739797
Nov. 24, 1987 [DE] Fed. Rep. of Germany ....... 3739800

[51] Int. Cl.$^5$ .............................................. C08G 63/12
[52] U.S. Cl. ................................... 528/206; 528/208; 528/271; 528/272; 528/335; 528/347; 568/633; 568/634

[58] Field of Search ............... 528/206, 208, 271, 272, 528/335, 347; 568/633, 634

[56] References Cited

U.S. PATENT DOCUMENTS 3,980,713  9/1976  Matsunaga et al. ................. 568/633

*Primary Examiner*—Maurice J. Welsh

[57] ABSTRACT

Partly fluorinated carboxylic acids and derivatives thereof, processes for their preparation and their use. Partly fluorinated carboxylic acids, in particular a partly fluorinated dicarboxylic acid, its acid chloride and partly fluorinated tetracarboxylic acids having various fluorine contents and their dianhydrides are obtained by atmospheric oxidation in an acid medium and at elevated temperature in the presence of a catalyst mixture of at least two heavy metal compounds and bromide ions. The compounds are used for the preparation of polycondensates and linear polycarboxylic acid amides and -carboxylic acid esters.

23 Claims, No Drawings

PARTLY FLUORINATED CARBOXYLIC ACIDS AND DERIVATIVES THEREOF, PROCESSES FOR THEIR PREPARATION AND THEIR USE

The invention relates to partly fluorinated carboxylic acids, in particular to a partly fluorinated dicarboxylic acid and the acid chloride thereof and to partly fluorinated tetracarboxylic acids with various fluorine contents and their anhydrides, processes for their preparation and their use.

The preparation of 1,1-bis-[4-(1,2-dicarboxyphenyl)]-1-phenyl-2,2,2-trifluoroethane from the corresponding 1,2-dimethylphenyl compound is known (CA 107: 97277 j (1987), NASA, Techn. Memory 87 113 (1985)). The oxidation was carried out with potassium permanganate and gave low yields and a contaminated, very hygroscopic product (3F-tetracarboxylic acid).

Dixylylhexafluoropropane (DX-F6) and its oxidation with potassium permanganate in a mixture of pyridine and water to give the potassium salt of 2,3-bis-(3,4-dicarboxyphenyl)-hexafluoropropane (6F-tetracarboxylic acid) is described in US-A 3,310,573. The type of oxidation necessitates a high requirement of chemicals, isolation of the tetracarboxylic acid is also very cumbersome here, and the solvent system used and the manganese oxide must be worked up.

The oxidation of 2,2-bis(4-methylphenyl)hexafluoropropane with atmospheric oxygen in an acetic acid medium in the presence of a catalyst of cobalt ions and bromine ions is known (SU-644 777 = CA 90:P 168310 K (1979)). The application of this reaction to fluorine-containing compounds which carry two hexafluoroisopropylidene bridges and in addition a diphenyl ether bridge was not obvious, however, since the ether bridge generally changes the reaction behavior during oxidation reactions. The application of this reaction to fluorine-containing compounds which have a 3,4-dimethylphenyl configuration failed, however, since the yield and purity of the resulting compounds were not satisfactory.

A process is furthermore known for the preparation of benzenetetracarboxylic acids and their anhydrides by oxidation of tetraalkyl-substituted benzenes with oxygen or gases containing free oxygen in the presence of heavy metal compounds and bromine compounds at elevated temperatures (DE-A 2,112,009). The publication shows that complete oxidation of two adjacent methyl groups presents considerable problems.

When the oxidation reaction has ended, non-oxidized methyl groups and CHO and CH₂OH groups are present in the reaction product. The CH₂OH group forms phthalide rings with the adjacent carboxyl group.

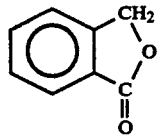

An additional difficult factor is that adjacent carboxyl groups can form stable compounds with heavy metals and precipitate as metal salts. This greatly reduces the catalytic activity of the catalyst. This metal salt formation is observed both with phthalic acid and with pyromellitic acid.

To prevent the drop in catalytic activity of the catalyst and to aid the oxidation in particular of a fourth alkyl group, it is necessary for large amounts of bromine ions to be present during the reaction. Application of this process to fluorine-containing compounds is said to be impossible since bromination reactions under the given experimental conditions give products with a high bromine content which are difficult to separate off and mean that the end product cannot be obtained in sufficient purity and yield. It has moreover been found that the partly fluorinated polycarboxylic acids do not crystallize out completely from the reaction solution, if at all, and moreover are partly mixed with their heavy metal salts, which make purification considerably more difficult.

This behavior is all the more surprising since polycarboxylic acids such as terephthalic acid, phthalic acid or pyromellitic acid crystallize out of the reaction medium, such as acetic acid, immediately and in a well-crystallized form.

Partly fluorinated tetracarboxylic acids with 12 fluorine atoms (12F-tetracarboxylic acid) are as yet unknown.

There was therefore the object of providing a process for partly fluorinated carboxylic acids which allows high yields and a high purity of the resulting products to be achieved. The partly fluorinated tetracarboxylic acids and their dianhydrides are thus, for example, units for polyimides which can be used for industrially important purposes, for example for coatings and adhesives exposed to high degrees of heat in aircraft construction or in microelectronics. For many of these fields of use it is therefore desirable to demand a high purity of the substances used, for example of 99% or more. The use of the compounds prepared by the process according to the invention in microelectronics also makes it necessary for all the metal ions which originate from the catalyst or are entrained during the reaction steps to be removed down to concentrations within the ppm range.

The highly selective oxidation should consist of as complete an oxidation as possible of all methyl groups in the methyl compounds and in prevention of side reactions, such as decarboxylation and condensation. In order to achieve this aim, special oxidation conditions must be found.

The invention relates to compounds of the formula

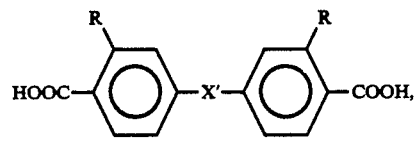

in which X' represents the radical

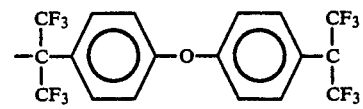

(= 12 F radical)
and thus forms the formula

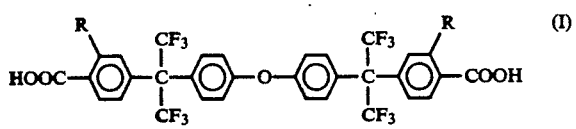

in which R represents hydrogen or —COOH, and the acid chloride, with the proviso that R is hydrogen, and the dianhydride, with the proviso that R represents the radical —COOH.

The invention also relates to a process for the preparation (a) of a compound of the formula

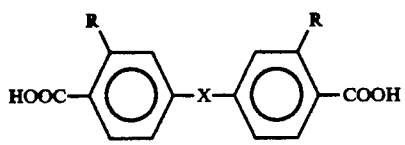

in which X denotes the groups

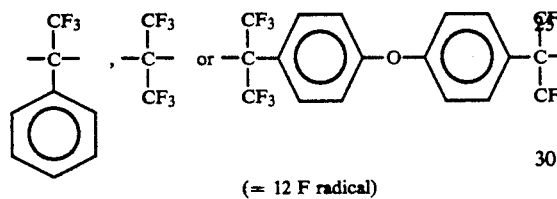

(= 12 F radical)

and R represents hydrogen or —COOH, with the proviso that X only represents the 12 F radical if R is hydrogen, or (b) the anhydride thereof, if R is other than hydrogen, or (c) the acid chloride, if R is hydrogen and X is the 12 F radical, by atmospheric oxidation in an acid medium under increased pressure and at elevated temperature in the presence of a catalyst mixture, which comprises oxidizing the corresponding methyl compound in an acid organic medium by passing in atmospheric oxygen at temperatures of 120° to 220° C. and under a pressure of between 5 and 40 bar in the presence of at least two heavy metal compounds and of bromide ions, and isolating the product as such or converting the resulting reaction product into the dianhydride (b) or into the acid chloride (c) of the compound of the formula (II).

The object of the invention was achieved by observing particular conditions for the oxidation of the methyl compounds. A conversion rate of the corresponding tetracarboxylic acids of more than 90% was achieved.

The following measures have proved favorable here:

(1) Catalyst:

(a) choice of the constituents for the catalyst, in particular $Co^{2+}$, $Mn^{2+}$, $Ce^{3+}$, $Br^-$ (b) optimum ratio of the metal ions with one another (c) high total metal concentration in the reaction solution (d) high concentration ratio of metal ions: bromide ions (2) Reaction conditions:

(a) high oxygen partial pressure
(b) controlled water content

The oxidation takes place in an acid organic medium in which the methylphenyl compounds are oxidized with molecular oxygen, the acid medium consisting to at least 40% of a monocarboxylic acid, such as acetic acid or propionic acid or mixtures thereof. Acetic acid is to be preferred because of its higher resistance towards oxidative degradation. The ratio of acid medium to starting substance employed can be up to a ratio of 40:60% by weight, based on the total reaction weight.

The diphenyl ethers 4,4'-bis[2-(4-methylphenyl)hexafluoroisopropyl]diphenyl ether and 4,4'-bis[2-(3,4-dimethylphenyl)hexafluoroisopropyl]diphenyl ether used to prepare the di- and tetracarboxylic acids with the 12 F radical are obtainable by a process which has been described in Patent Application ... which has been filed on the same day and corresponds to German Patent Application P 37 39 795.8, title "Partly fluorinated diphenyl ethers, processes for their preparation and their use".

The catalyst mixture consists of at least two heavy metal salts and bromide ions. Heavy metals which are used are, for example, cobalt, manganese or cerium, the presence of cobalt always being necessary. In the preparation of the dicarboxylic acid, for example, a mixture of cobalt and manganese ions which can additionally contain cerium ions is used. By mixing the metal salts, the total metal concentration can be kept lower than if only cobalt alone is used.

Bromide ions are absolutely essential for the complete course of the oxidation. If a mixture of cobalt and manganese ions is used as the metal component, the metals are in general used in a molar ratio of 3:1 to 1:3, preferably 1:1. The sum of the concentrations of the two elements is in general 0.01 to 0.2, preferably 0.02 to 0.12 and in particular 0.04 to 0.08 gram atom/kg total weight. The molar ratio of the sum of cobalt and manganese to bromine is in general 1 : (0.01 to 0.8), preferably 1:(0.05 to 0.4). In the preparation of the dicarboxylic acid, it is in general 1:(0.01 to 2), preferably 1:(0.025 to 1) and in particular 1:(0.05 to 0.2). As already mentioned, it is possible to use cerium ions in addition to the two metal ions of the catalyst. These catalyze the oxidation of incompletely oxidized intermediate stages. Their presence increases the purity and yield of the partly fluorinated carboxylic acids. The cerium ions are added to the catalyst in a molar ratio of the sum of cobalt and manganese ions to cerium ions of 1:(0.02 to 1.2), preferably 1:(0.05 to 0.6). In the case of the dicarboxylic acids, the ratio is 1:(0.02 to 2), preferably 1:(0.05 to 1) and in particular 1:(0.2 to 0.6). If a mixture of the metal ions of cobalt and cerium is used, the molar ratio of the two metals is in general 1:(0.02 to 1.2), the ratio of the metals to bromine being as described above. The molar ratios always relate to the total weight, that is to say the sum of the compound to be oxidized, solvent and catalyst. The metal ions are preferably employed in the form of their acetates.

Bromine can be employed in the form of bromides, for example the bromides of the alkali metals, including ammonium bromide, and those of the metals cobalt, manganese and cerium, or as a solution of hydrogen bromide in water or glacial acetic acid. In addition, bromine-containing organic compounds which dissociate during the reaction and release bromine ions, for example tetrabromomethane, can also be used. The bromide ion concentration in the reaction solution can be greatly reduced—down to a value of about 20 for the molar ratio of $\Sigma M^n:Br$ (sum of metal ions to bromine ions)—without there being a noticeable drop in the rate of reaction. The undesirable nuclear bromination is greatly decreased by this measure, which at the same time also increases the ratio of tetramethyl compounds: Br in the reaction solution.

The oxidation is in general carried out at temperatures from 120 to 220, preferably 140 to 190 and in particular 155° to 180° C. The pressure in the reactor is in general between 5 and 40, preferably between 10 and 30 and in particular between 14 and 20 bar.

For the procedure, it is advantageous for the air required for the oxidation to be introduced into the liquid phase close to the bottom of the reactor and to be finely dispersed in the liquid phase by vigorous stirring or by special jets. It is particularly advantageous to introduce an oxidation mixture in which the oxygen content has been increased to a content of more than 21% by volume by admixing with pure oxygen. High oxygen partial pressures in the gas bubbles entering the liquid phase are achieved by this measure. It is advantageous for the oxygen partial pressure at the discharge point of the introduction device to be at least 1 bar, preferably 2 to 15 and in particular 3 to 10 bar.

It is furthermore advantageous for carrying out the procedure if the residual oxygen content of the exhaust gas does not fall below certain values. The oxygen partial pressure is defined by the formula $$P_{O_2} = \% \text{ by volume of } O_2 \times (P_{tot} - P_{ac\ vapor\ pressure})$$

that is to say it is the mathematical product of the residual oxygen content and the difference between the total pressure and the acetic acid vapor pressure (ac vapor pressure) at the prevailing reaction temperature. This oxygen partial pressure in the gas phase above the reaction solution should not fall below 0.2 bar and is preferably between 0.35 and 2.8, in particular between 0.45 and 1.3 bar.

When the highly exothermic reaction has ended, it is advantageous to keep the reactor at 150° to 190° C., preferably 160° to 180° C., under an oxygen partial pressure of 0.4 to 2 bar, preferably 0.5 to 1.3 bar, for 1 to 3 hours, preferably for 2 hours, to bring the oxidation of all the methyl groups to completion.

The water concentration of the acid medium in which the reaction is carried out has a considerable influence on the procedure of the process according to the invention. Although the tetramethyl compounds can also be oxidized in—for example—acetic acid with a water concentration of 15% or more, the yield and above all the purity of the resulting products is in this case reduced and oxidation of all four methyl groups proceeds only incompletely. On the other hand, it has been found that in anhydrous acetic acid the metal ions of the catalyst are precipitated and therefore inactivated by the tetracarboxylic acids. The range for the water concentration in which the metal ions remain dissolved and in which the oxidation proceeds sufficiently completely is between 2 and 12, preferably between 2 and 7 and in particular between 3 and 5% of water in the monocarboxylic acid, i.e. acetic acid.

It has been found, surprisingly, that the dianhydrides of the tetracarboxylic acids are sparingly soluble in glacial acetic acid or mixtures of glacial acetic acid and acetic anhydride if the water is removed from the reaction solution by suitable methods and the tetracarboxylic acids are converted into their anhydrides. This conversion can be effected by distillation and/or by addition of acetic anhydride. The dianhydrides crystallize in a high yield and in a form which can readily be filtered and were freed from the metal salts and the soluble by-products by washing with glacial acetic acid, preferably a mixture of glacial acetic acid and acetic anhydride. Washing with a mixture of glacial acetic acid and acetic anhydride is particularly suitable, since this mixture prevents caking of the filter cake. The dianhydrides are obtained in a purity of 94 to 97%.

Surprisingly, the metal salts also dissolve during the anhydride formation, so that the content of all metal ions is already 50 to 100 ppm after this first purification operation.

The conversion of the tetracarboxylic acids is preferably carried out by distilling off a mixture of acetic acid and water from the reaction solution and then adding a small excess of acetic anhydride over the calculated amount of acetic anhydride (about 3 to 12% of acetic anhydride in the solution) under the influence of heat.

A particular process variant comprises distilling off water from the reaction solution over a column at elevated temperature and under pressure. Under these conditions, the dianhydrides of the tetracarboxylic acids are likewise formed, water being split off. At the same time, the metal salts are also dissolved again. To bring the conversion to the dianhydride to completion, acetic anhydride is finally added in an amount so that the solution contains about 3 to 12% of acetic anhydride.

The formation of dianhydride by removal of water by distillation is preferably carried out at a temperature above 140° C., if necessary under the additional pressure of an inert gas. All or some of the acetic acid can also be replaced by another aliphatic carboxylic acid, such as propionic acid, hexanoic acid or 2-ethylhexanoic acid.

In general, the filtered and washed dianhydrides are dried in a stream of air, preferably under reduced pressure, at elevated temperature.

An inorganic or organic acid, for example hydrochloric acid, is advantageously used during isolation as the tetracarboxylic acid. The tetracarboxylic acids can advantageously be crystallized from water in a readily filterable form if small concentrations of acetic acid, preferably 6 to 12% by weight of acetic acid, are dissolved therein. In general, a procedure is followed in which, when the oxidation has ended, acetic acid is distilled off from the reaction solution until the bottom temperature is about 130° to 155° C. and the melt is still easily stirrable. Hot water and if appropriate acid are added to the hot melt and the solution is heated once more, preferably under pressure, at 130° to 150° C. for up to 2 hours.

The tetracarboxylic acids crystallize as the hydrate and can be isolated as the hexahydrate by careful drying at room temperature. They are converted into the tetracarboxylic acids by heating at 50° to 80° C. in a stream of gas and into the dianhydrides by heating at 180° to 190° C. under reduced pressure.

Particularly pure products are obtained when the still water-moist tetracarboxylic acid is suspended in a solvent and the water is distilled off. The hydrate-free tetracarboxylic acid is first formed, and the dianhydride is formed from this by further increasing the temperature.

Aromatic solvents, such as toluene, o-xylene, tetrahydrois naphthalene, acetophenone or diphenyl ether, are particularly suitable.

The formation of anhydride in aromatic solvents can be accelerated considerably by addition of catalytic amounts of carboxylic acids, for example aliphatic carboxylic acids, such as acetic acid or 2-ethylhexanoic acid, or other acids, such as toluenesulfonic acid.

For conversion into the acid chloride, the dicarboxylic acid obtained by the process according to the invention is treated in a known manner, for example with thionyl chloride, and obtained from the reaction solution by known methods. The dicarboxylic acid and its acid chloride can be used for the preparation of linear polycarboxylic acid amides and -carboxylic acid esters, which in the form of molded articles, films and fibers have a high heat stability, excellent mechanical properties, good transparency, good dirt-repellancy properties and a resistance to radiation.

The tetracarboxylic acids can be used for the preparation of polycondensates, such as polyimides, polycarboxylic acid amides, polyamidocarboxylic acid esters, polyamides and imide oligomers, which, amongst other things, have low melting points, a high solubility, low dielectric constants and an increased heat stability.

In the following examples, % always means percentage by weight.

EXAMPLES

(1)

1,1-Bis-(3,4-dicarboxyphenyl)-1-phenyl-2,2,2-trifluoroethane (3F-tetracarboxylic acid)

A mixture of 148.3 g of 1,1-bis-(3,4-dimethylphenyl)-1-phenyl-2,2,2-trifluoroethane, 2.49 g of $Co(OAc)_2 \cdot 4H_2O$, 2.45 g of $Mn(OAc)_2 \cdot 4H_2O$, 0.41 g of HBr, corresponding to 4.1 g of a 10% strength HBr solution in glacial acetic acid, and 550 g of glacial acetic acid was heated to 180° to 185° C. under an oxygen pressure of 7.5 bar. From about 100° C., the exothermic reaction started and lasted for about 85 minutes. The temperature was then kept at 176° C. for a further hour. 784 g of solution resulted. About 530 g of acetic acid-water were distilled off from the reaction solution over a descending condenser, with stirring, during which the bottom temperature rose to 145° C. 150 g of water at 80° C. were added to the hot melt, 50 ml of concentrated hydrochloric acid were added to the mixture and the mixture was heated at the boiling point for one hour. It was cooled, with vigorous stirring, and the batch was seeded with crystals of the 3F-tetracarboxylic acid. The resuspended crystals were filtered off with suction and washed four times with 50 ml of 2 N hydrochloric acid and twice with 25 ml of water. The moist crystals were dried in a stream of air at 50° C./64 mbar.

Yield: 190.4 g (96.8% of theory) of 3F-tetracarboxylic acid, melting point 210° to 213° C., removal of water; carboxyl group content: 8.08 meq of COOH/g (calculated 8.20)

(2)

1,1-Bis-(3,4-dicarboxylphenyl)-1-phenyl-2,2,2-trifluoroethane-dianhydride (3F-dianhydride)

400 g of an acetic acid-water mixture were distilled off from a reaction solution of the same oxidation batch as in Example 1 over a descending condenser, with stirring. A mixture of 122.4 g of acetic anhydride and 120 g of glacial acetic acid was then added dropwise at the boiling point in the course of half an hour and the mixture was boiled under reflux for one hour. On cooling, with stirring, crystallization started at below 85° C.. After 4 hours, the crystals were filtered off with suction and washed three times with 25 ml portions of a mixture of 95% of glacial acetic acid and 5% of acetic anhydride. The crystals were dried at 80° C./65 mbar in a gentle stream of air.

Yield: 119.0 g (65.3% of theory) of 3F-dianhydride, yellowish crystals; melting point: 204 to 205.5° C.

A further 36.6 g (20.1% of theory) of 3F-dianhydride with a melting point of 201° to 204° C. were obtained from the combined filtrates.

(3) 2,2-Bis-(3,4-dicarboxyphenyl)-hexafluoropropane (6F-tetracarboxylic acid)

A solution of 2.5 g of cobalt acetate tetrahydrate, 2.45 g of manganese acetate tetrahydrate and 0.44 g of hydrogen bromide in 311 g of glacial acetic acid was introduced into a 1 l glass autoclave fitted with a metering pump, thermometer, stirrer and reflux condenser. Parallel to this, a solution of 180.2 g of dixylylhexafluoropropane in a mixture of 102 g of acetic anhydride and 60 g of glacial acetic acid was prepared in a metering device. The autoclave was placed under a total pressure of 7.5 bar by passing in oxygen, an exhaust gas value of 30 Nl/h (Nl=normal liter) was established and the contents were heated. Metering in of dixylylhexafluoropropane was started at about 160° C. and the total amount was added within 100 minutes. The temperature of the exothermic reaction was kept at 170° to 175° C., and when the metering had ended the batch was kept at 175° C. for a further hour by heating. About 500 g of an acetic acid-water mixture were distilled off from the reaction mixture (about 790 to 800 g) under normal pressure. As soon as the temperature of the residue had risen to 145° C., the autoclave was placed under a pressure of 4 bar by passing in nitrogen, 500 g of distilled water were added and the mixture was kept at 145° C. for one hour. It was then cooled to room temperature and the crystal flakes formed were filtered off with suction. The mother liquor contained 6 to 10% of acetic acid. The filter cake was washed 8 times with 50 ml of ice-water each time. The moist product, which consisted of 6F-tetracarboxylic acid hexahydrate and adhering water, was dried in a stream of air at 40 to 50° C./50 mbar for 8 hours. The temperature was then increased to 80° C. and the solid was dried for a further 12 hours. Yield of 212.3 g (88.4% of theory) of 6F-tetracarboxylic acid, melting point: 231 to 234° C. (removal of water), carboxyl group content: 8.45 meq of COOH/g (calculated 8.33), bulk density 0.30 g/$cm_2$, residual ion content (micrograms/g): cobalt 1, manganese 1, bromine 189.

(4)

2,2-Bis-(3,4-dicarboxyphenyl)-hexafluoropropanedianhydride 2.24 g of cobalt acetate tetrahydrate, 2.21 g of manganese acetate tetrahydrate and 0.365 g of hydrogen bromide in 302 g of glacial acetic acid were reacted with a solution of 142.6 g of dixylylhexafluoropropane in 125 g of glacial acetic acid in accordance with the procedure in Example 3. The oxygen pressure was 8 bar and the reaction temperature during the oxidation was kept in the range from 165° to 175° C. Acetic acid and water were distilled off from the resulting reaction solution, with stirring, until a bottom temperature of 130° C. was reached. A mixture of 92 g of acetic anhydride and 200 g of glacial acetic acid was then added at this temperature in the course of 20 minutes. The liquid containing about 5% by weight of acetic anhydride was boiled under reflux for one hour, cooled to 20° C. and stirred at this temperature for 2¼ hours. After filtering off with suction, the filter cake was washed eight times with 50 g of a mixture of glacial acetic acid and acetic anhydride (95:5) and the resulting crystals were dried in a weak stream of air at 100° C. under 60 mbar. Yield of 165.5 g (94.7%) of colorless crystals, start of sintering 237° C., melting point: 242 to 243° C., purity 95.8% of 6F-dianhydride, contamination by traces of catalyst: 10 ppm of cobalt, 6 ppm of manganese, 215 ppm of bromine.

(5) 6F-Dianhydride from 6F-tetracarboxylic acid 212.3 g of 6F-tetracarboxylic acid were agitated in the flask of a rotary evaporator in an oil bath at 190° C.. The steam formed was displaced from the flask by a gentle stream of air. 15.1 g of water were collected in a cold trap. Yield 198.5 g of 6F-dianhydride, melting point 242 to 243.5° C., anhydride groups 4.51 mbar (calculated 4.50).

(6) 6F-Dianhydride from water-moist 6F-tetracarboxylic acid 342.2 g of water-moist 6F-tetracarboxylic acid obtained according to Example 3 were suspended in 700 g of tetrahydronaphthalene in a flask fitted with a stirrer and water separator. The batch was heated, while stirring vigorously, and about 125 g of water were distilled off. The temperature was then increased to the boiling point and tetrahydronaphthalene, which still carried residues of the water split off, was slowly distilled off. The anhydride formation had ended when no further water was separated off. The crystals which separated out were washed with tetrahydronaphthalene at 20° C. and dried at 100° C. under reduced pressure. Yield 206.4 g (85.9% of theory), purity 99.9%, melting point: 243° to 245° C..

The superiority of the process according to the invention is clearly demonstrated in the following Examples 7 to 31, which were carried out under the conditions and by the procedure of Example 4. Examples 7 to 13 (Table 1) thus illustrate the influence of the catalyst composition. Products of high purity are obtained in a good yield under the conditions according to the invention.

The influence of the ion concentration and of the ratio of cobalt to manganese is demonstrated in Examples 14 to 20 (Table 2). It can be seen that at a low total metal ion concentration although an increase in the bromine ion concentration increases the yield, this cannot be brought to the level obtained by the measures of the invention. Examples 21 to 25 (Table 3) also reflect once again the influence of the bromide ion concentration. The higher this is, the greater is the content of organically bonded bromine in the end products. If the ratio of the sum of the metal ions to the bromine ions is very high, the yield drops considerably. Examples 26 to 31 (Table 4) illustrate that the water concentration already causes a distinct drop in yield at a water content of 15%.

The amounts of substances required for the reaction can be obtained from the total weight of the batch and the concentrations given in the table. These concentrations of the substances are in [mol/kg] and are based on the total weight of all the reaction constituents employed (apart from $O_2$). The acetic acid is obtained here as the remaining amount to make up the total weight, for example the amount of dixylylhexafluoropropane (DX-F6) of 0.396 mole or 142.7 g corresponds to the value $C_{DX-F6}=0.66$ mole/kg in the table at a total weight of 0.6 kg. As in Example 4, the DX—F6 is metered in during the reaction. ⅓ of the total amount of acetic acid is used to prepare this solution.

EXAMPLES (7) to (13)

Influence of the catalyst composition

The product quality relates to the sintering and melting point of a compound. The higher these values, the purer the compound.

TABLE 1

| | No: | | | | | | |
|---|---|---|---|---|---|---|---|
| | 7 (Comparison) | 8 (Comparison) | 9 (Comparison) | 10 | 11 | 12 | 13 (Comparison) |
| $C_{DX-F6}$ [Mol/kg] | 0.66 | 0.66 | 0.66 | 0.66 | 0.66 | 0.66 | 0.66 |
| $C_{Co}$ [Mol/kg] | — | 0.0150 | 0.0600 | 0.0300 | 0.0150 | 0.0150 | — |
| $C_{Mn}$ [Mol/kg] | 0.0600 | — | — | 0.0300 | 0.0150 | — | 0.0150 |
| $C_{Ce}$ [Mol/kg] | — | — | — | — | 0.0150 | 0.0150 | 0.0150 |
| $\Sigma C_{Metal}$ [Mol/kg] | 0.0600 | 0.0150 | 0.0600 | 0.0600 | 0.0450 | 0.0300 | 0.0300 |
| $C_{Br}$ [Mol/kg] | 0.0150 | 0.0075 | 0.0150 | 0.0150 | 0.0075 | 0.0075 | 0.0075 |
| Crude yield [% of theory] | 26.5 | 30.8 | 80.5 | 96.2 | 96.2 | 95.0 | <15 |
| mp. [°C.] | 233–235 | 231–234 | 224–236 | 241–242 | 242–244 | 238–241 | — |
| Sintering [°C.] | 231 | 218 | 203 | 236 | 237 | 229 | — |
| Purity [%] | 82 | 85 | 83 | 95.2 | 98.5 | 93.7 | — |

EXAMPLES (14) TO (20)

Dependence of the yield and product quality on the total ion concentration and on the ratio [Co]:[Mn].

TABLE 2

| | No. | | | | | | |
|---|---|---|---|---|---|---|---|
| | 14 (Comparison) | 15 (Comparison) | 16 | 17 | 18 | 19 | 20 |
| $C_{DX-F6}$ [Mol/kg] | 0.66 | 0.66 | 0.66 | 0.66 | 0.66 | 0.66 | 0.66 |
| $C_{Co}$ [Mol/kg] | 0.0050 | 0.0050 | 0.0075 | 0.0150 | 0.0225 | 0.0150 | 0.0075 |
| $C_{Mn}$ [Mol/kg] | 0.0050 | 0.0050 | 0.0075 | 0.0075 | 0.0075 | 0.0150 | 0.0225 |
| $\Sigma C_{Metal}$ [Mol/kg] | 0.0100 | 0.0100 | 0.0150 | 0.0225 | 0.0300 | 0.0300 | 0.0300 |
| $C_{Br}$ [Mol/kg] | 0.0025 | 0.0100 | 0.0038 | 0.0056 | 0.0075 | 0.0075 | 0.0075 |
| $C_{Co}:C_{Mn}$ | 1:1 | 1:1 | 1:1 | 2:1 | 3:1 | 1:1 | 1:3 |
| Crude yield [% of theory] | 42.8 | 77.4 | 95.0 | 95.7 | 64.4 | 94.9 | 95.1 |
| mp. [°C.] | 237–239 | 235–237 | 242–243 | 243–245 | 235–238 | 242–243 | 236–240 |
| Sintering [°C.] | 234 | 233 | 238 | 237 | 222 | 237 | 222 |

EXAMPLES (21) TO (25)

Influence of the bromide concentration on the yield and product quality

TABLE 3

| | No. | | | | |
|---|---|---|---|---|---|
| | 21 (Comparison) | 22 | 23 | 24 | 25 (Comparison) |
| $C_{DX-F6}$ [Mol/kg] | 0.68 | 0.66 | 0.68 | 0.68 | 0.68 |
| $C_{Co}$ [Mol/kg] | 0.0300 | 0.0150 | 0.0280 | 0.0300 | 0.0300 |
| $C_{Mn}$ [Mol/kg] | 0.0300 | 0.0150 | 0.0280 | 0.0300 | 0.0300 |
| $\Sigma C_{Metal}$ [Mol/kg] | 0.0600 | 0.0300 | 0.0560 | 0.0600 | 0.0600 |
| $C_{Br}$ [Mol/kg] | 0.0600 | 0.0075 | 0.0080 | 0.0038 | 0.0015 |
| $C_{DX-F6}/C_{Br}$ | 11.3 | 88 | 85 | 179 | 453 |
| $\Sigma C_M/C_{Br}$ | 1:1 | 4:1 | 7:1 | 16:1 | 40:1 |
| Crude yield [% of theory] | 94.7 | 94.9 | 92.7 | 94.2 | 71.2 |
| mp. [°C.] | 239.5–241 | 242–243 | 242–244 | 241–243 | 236–240 |
| Sintering [°C.] | 235 | 237 | 238 | 236 | 229 |
| Organically bonded bromine [ppm] | 670 | 215 | 152 | 142 | 121 |
| Purity [%] | 95.0 | 95.8 | 98.8 | 96.4 | 93.8 |

EXAMPLES (26) TO (31)

Influence of the water concentration in the acetic acid on the yield and purity of the product

TABLE 4

| | No. | | | | | |
|---|---|---|---|---|---|---|
| | 26 | 27 | 28 | 29 | 30 | 31 (Comp.) |
| Initial $H_2O$ concentration [%] | 0.4 in 302.5 g acetic acid | 0.54 in 298 g acetic acid | 3.4 in 302.5 g acetic acid | 4.4 in 303 g acetic acid | 8.4 in 303 g acetic acid | 15.4 in 303 g acetic acid |
| Amount of glacial acetic acid anhydride metered with DX-F6 | 150 g Ac | 98.9 g Ac$_2$O 49.4 g Ac | 132.7 g Ac$_2$O 25.0 g Ac | 150 g Ac | 175 g Ac | 175 g Ac |
| Final $H_2O$ concentration | 6.2% 6.5% | 2.7% 3.7% | 3.1% 4.4% | 8.7% 9.3% | 10.7% 10.1% | 14.9% 14.0% |
| mp. [%] | 242–243 | 242–244 | 242–244 | 241–243 | 239–242 | 222–236 |
| Sintering [°C.] | 237 | 239 | 234 | 227 | 224 | 193 |
| Purity [%] | 95.8 | 98.4 | 97.2 | 93.6 | 91.9 | 85.7 |
| Crude yield [% of theory] | 94.7 | 93.0 | 95.0 | 95.3 | 94.9 | 82.4 |
| Pure yield | 90.7 | 91.5 | 92.3 | 89.2 | 87.2 | 70.6 |

TABLE 4-continued

| | No. | | | | | |
|---|---|---|---|---|---|---|
| | 26 | 27 | 28 | 29 | 30 | 31 (Comp.) |
| [% of theory] | | | | | | |

Ac = Glacial acetic acid
Ac₂O = Acetic anhydride

(32) 4,4'-Bis[2-(carboxyphenyl)hexafluoroisopropyl]-diphenyl ether 250 g of 4,4'-bis[2-(4-methylphenyl)hexafluoroisopropyl]-diphenyl ether, 2.49 g of Co(OAc)$_2$.4H$_2$O, 2.45 g of Mn(OAc)$_2$.4H$_2$O, 0.41 g of HBr=4.1 g of a 10% strength HBr solution in glacial acetic acid and 550 g of glacial acetic acid were introduced into a 1 l glass autoclave fitted with a stirrer, gas inlet tube, thermometer and reflux condenser. The mixture was heated up to a maximum of 180° C. under an oxygen pressure of 7.5 bar. The exothermic reaction started at about 130° C., with uptake of oxygen, and lasted 40 minutes. The final temperature of 175° C. was maintained for a further hour. 300 g of acetic acid were distilled off from the reaction solution, which was cooled to about 100° C., and the distillation residue was cooled to 20° C., while stirring. The suspended crystals formed were filtered off over a suction filter. The filter cake was washed with four portions of 15 ml of glacial acetic acid and then with five portions of 40 ml of water. The moist product was dried in a gentle stream of air at 70° C./65 mbar. Yield: 211.8 g (77.6% of theory), melting point: 238°-240° C., colorless crystals, carboxyl group content: 2.84 meq of COOH/g (calculated 2.82). Additional product precipitated out of the mother liquor by addition of the washing water. 57.3 g (21.0% of theory), melting point: 227°-232° C.

| Analysis: C$_{32}$H$_{18}$F$_{12}$O$_5$ | | | |
|---|---|---|---|
| calculated: | C 54.08% | H 2.53% | F 32.11% |
| found: | C 54.00% | H 2.60% | F 32.00% |

(33) 4,4'-Bis[2-(4-chlorocarbonylphenyl)hexafluoroisopropyl]-diphenyl ether

A few drops of dimethylformamide were added to a suspension of 4,4'-bis[2-(4-carboxyphenyl)-hexafluoroisopropyl]-diphenyl ether in thionyl chloride and the mixture was heated under reflux conditions until the evolution of hydrogen chloride had ended. The excess thionyl chloride was stripped off and toluene was added in order to remove the remaining thionyl chloride by distillation. When the toluene had been removed, the crude product was recrystallized from n-hexane. Melting point: 144°-145° C..

(34) (a) 4,4'-Bis[2-(3,4-dicarboxyphenyl)hexafluoroisopropyl]-diphenyl ether (12F-tetracarboxylic acid)

200.3 g of 4,440 -bis[2-(3,4-dimethylphenyl)hexafluoroisopropyl]diphenyl ether, 2.49 g of Co(OAc)$_2$.4H$_2$O, 2.45 g of Mn(OAc)$_2$.4H$_2$O, 0.41 g of HBr, corresponding to 4.1 g of 10% strength HBr solution in glacial acetic acid, and 550 g of glacial acetic acid were introduced into to a 1 l glass autoclave fitted with a stirrer, gas inlet tube, thermometer and reflux condenser. The mixture was heated up to a maximum of 188° C. under an oxygen pressure of 7.5 bar. The exothermic reaction started at between 90° and 100° C., with uptake of oxygen, and lasted 65 minutes. The final temperature of 177° C. was maintained for a further 1¼ hours. 816 g of solution were isolated.

(b) The reaction solution was cooled to 90° C. and filtered, the filtrate was transferred to a 2 l four-necked flask with a stirrer and acetic acid was distilled off until the bottom temperature was 140° C. 1 liter of water at 95° C. were added to the violet melt, whereupon an emulsion formed. 200 ml of concentrated hydrochloric acid were added at 80° C., while stirring at a high speed. The emulsion was seeded with crystals of 12 F-tetracarboxylic acid at 75° C., a suspension of crystals forming on cooling.

The suspended crystals were filtered off over a suction filter at 22° C. and washed twice with 200 ml portions of 2N hydrochloric acid and once with 200 ml of water and the water-moist substance was dried in a gentle stream of air at 60° C./65 mbar.

Yield: 227.2 g (96.4%) of 12 F-tetracarboxylic acid, colorless crystals, melting point 163° to 165° C., with removal of water, carboxyl group content: 5.06 meq of COOH/g (calculated 5.01).

| Analysis for C$_{34}$H$_{18}$F$_{12}$O$_9$: | | | |
|---|---|---|---|
| calculated: | C 51.13% | H 2.26% | F 28.57% |
| found: | C 51.00% | H 2.20% | F 28.35% |

(35) 12F-Tetracarboxylic acid dianhydride

A solution of 3.02 g of oxalic acid dihydrate in 30 ml of glacial acetic acid was added dropwise to the reaction solution from Example 34a), at 95° C. with stirring. After two hours under reflux, the hot solution at 100° C. was filtered and the filtrate was washed with 200 ml of hot acetic acid. 590 g of acetic acid and water were distilled off from the filtrate. 72.3 g of acetic anhydride were added dropwise to the residue at above 80° C. in the course of 30 minutes, while stirring at a high speed. The temperature rose to 120° C. and was kept at this value for one hour (12% of acetic anhydride in the acetic acid). On cooling, crystallization star i below 60° C.. The temperature was reduced further to 20° C. in the course of 6 hours. The resulting suspended crystals were filtered off over a suction filter and washed three times with 25 ml portions of a mixture of 90% of acetic acid and 10% of acetic anhydride and the filter cake was dried in a gentle stream of air at 60° C./65 mbar. Yield: 179.2 g (79.6% of theory) of 12F-dianhydride, melting properties: phase transition: 115°-120° C. with melting and renewed solidification, melting point: 168°-170° C., anhydride group content after titration with N/10 sodium hydroxide solution/N/10 hydrochloric acid: 2.625 meq of COOH/g (calculated 2.625).

| Analysis for $C_{34}H_{14}F_{12}O_7$: | | | |
|---|---|---|---|
| calculated: | C 53.54% | H 1.84% | F 29.92% |
| found: | C 53.40% | H 2.00% | F 29.30% |

We claim:
1. A compound of the formula

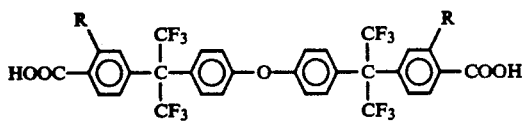

in which R represents hydrogen or —COOH, and the acid chloride of the compound of formula (I) with the proviso that R is hydrogen, and the dianhydride of the compound of formula (I) with the proviso that R represents the radical —COOH.

2. A process for the preparation
(a) of a compound of the formula

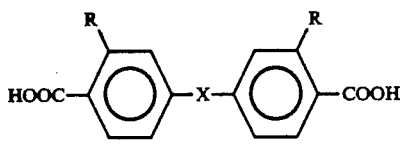

in which X denotes the groups

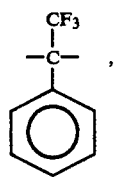

III

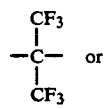 or

IV

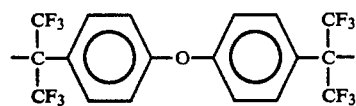

V and R represents hydrogen or —COOH, with the proviso that X only represents group V if R is hydrogen, or
(b) of the anyhydride of the compound of formula II, if R is other than hydrogen, or
(c) the acid chloride of the compound of formula II, if R is hydrogen and X is group V,
by atmospheric oxidation in an acid medium under increased pressure and at elevated temperature in the presence of a catalyst mixture, which comprises oxidizing the corresponding methyl compound in an acid organic medium by passing in atmospheric oxygen at temperatures of 120° to 220° C. and under a pressure of between 5 and 40 bar whereby the oxygen partial pressure at the inlet point of the oxygen is at least 1 bar, in the presence of at least two heavy metal compounds and of bromide ions, and isolating the product as such or converting the resulting reaction product into the dianhydride (b) or into the acid chloride (c) of the compound of the formula (II).

3. The process as claimed in claim 2, wherein acetic acid and/or propionic acid are used.

4. The process as claimed in claim 2, wherein the reaction temperature is 140° to 190° C.

5. The process as claimed in claim 2, wherein a pressure of between 10 and 30 bar is applied.

6. The process as claimed in claim 2, wherein the atmospheric oxygen used for the oxidation has an oxygen content of more than 21% by volume and the oxygen partial pressure at the inlet point of the oxygen is 2 to 15.

7. The process as claimed in claim 2, wherein the oxygen partial pressure in the gas phase above the reaction medium, which is given by the formula $P_0 = \%$ by volume of $O_2$ ($P_{total} - P_{acetic\ acid\ vapor\ pressure}$), is at least 0.2 bar.

8. The process as claimed in claim 2, wherein cobalt, manganese and/or cerium are used as heavy metal ions and these are added in the form of acetate compounds.

9. The process as claimed in claim 2, wherein bromine is used in the form of bromides or as a solution of hydrogen bromide in water or glacial acetic acid.

10. The process as claimed in claim 2, wherein the molar ratio of cobalt to manganese is 3:1 to 1:3, the sum of the concentrations of the two elements cobalt and manganese being 0.01 to 0.20 gram atom/ kg total reaction weight.

11. The process as claimed in claim 2, wherein the molar ratio of the sum of cobalt and manganese to bromine is 1:(0.01 to 0.8), or, if R is hydrogen and X is the 12 F radical in formula (II), the molar ratio is 1:(0,01 to 2).

12. The process as claimed in claim 2, wherein the catalyst contains, as an additional metal ion, cerium in a molar ratio of the sum of cobalt and manganese to cerium of 1:(0.02 to 1.2) or, if R is hydrogen and X is the 12 F radical, in the molar ratio of 1:(0.02 to 2).

13. The process as claimed in claim 2, wherein the molar ratio of cobalt to cerium is 1:(0.02 to 1.2) if R is the —COOH group in formula (II).

14. The process as claimed in claim 2, wherein the reaction batch is kept at 150° to 190° C. under an oxygen partial pressure of 0.4 to 2 bar for 1 to 3 hours after the exothermic reaction has ended, if R is the —COOH group in formula (II).

15. The process as claimed in claim 2, where reaction is carried out at a water concentration of the monocarboxylic acid of 2 to 12 %, if R is the —COOH group in formula (II).

16. The process as claimed in claim 2, wherein the dianhydride is formed using a small excess of acetic anhydride.

17. The process as claimed in claim 2, wherein the anhydride is formed by removal of water from the reaction solution by distillation at a temperature above 140° C., if appropriate under pressure.

18. The process as claimed in claim 17, wherein acetic anhydride is added up to a content of 3 to 12% in the solution in order to bring the reaction to completion.

19. The process as claimed in claim 2, wherein the dianhydride is prepared by heating the tetracarboxylic acid 180° to 190° C. under reduced pressure.

20. The process as claimed in claim 2, wherein the dianhydride is formed by removal of the water by distillation from the water-moist tetracarboxylic acid which is suspended in a water-immiscible solvent.

21. The process as claimed in claim 20, wherein toluene, o-xylene, tetrahydronaphthalene, acetophenone or diphenyl ether is used as the solvent.

22. Polycondensates, in the form of polyimides, polycarboxylic acid amides, polyamidocarboxylic acid esters, polyamides and imide oligomers prepared from a compound as claimed in claim 1, in which, R is COOH.

23. Linear polycarboxylic acid amides and -carboxylic acid esters, in the form of molded articles, films and fibers therefrom prepared from a compound as claimed in claim 1, in which R is hydrogen.

* * * * *

UNITED STATES PATENT AND TRADEMARK OFFICE
CERTIFICATE OF CORRECTION

PATENT NO. : 5,004,797
DATED : April 2, 1991
INVENTOR(S) : Rohrscheid et al.

It is certified that error appears in the above-identified patent and that said Letters Patent is hereby corrected as shown below:

In claim 7, col. 16, lines 16-17 the formula for the oxygen partial pressure should read
--$P_{O_2}$ = % by volume of $O_2$ X (Ptotal - P acetic acid vapor pressure)--

Signed and Sealed this

Twentieth Day of October, 1992

*Attest:*

DOUGLAS B. COMER

*Attesting Officer*    *Acting Commissioner of Patents and Trademarks*